United States Patent [19]

Tobe et al.

[11] E Re. 30,971

[45] Reissued Jun. 15, 1982

[54] COMPOSITIONS CONTAINING PLATINUM

[75] Inventors: Martin L. Tobe, Northwood, England; Abdul R. Khokhar, Burlington, Vt.; Peter D. M. Braddock, Maidenhead, England

[73] Assignee: Rustenburg Platinum Mines Limited, Johannesburg, South Africa

[21] Appl. No.: 119,656

[22] Filed: Feb. 20, 1980

Related U.S. Patent Documents

Reissue of:

[64] Patent No.: 4,119,654
Issued: Oct. 10, 1978
Appl. No.: 770,313
Filed: Feb. 22, 1977

[30] Foreign Application Priority Data

Feb. 26, 1976 [GB] United Kingdom ..... 7650/76

[51] Int. Cl.[3] ..... C07F 15/00
[52] U.S. Cl. ..... 260/429 R; 424/287
[58] Field of Search ..... 260/429 R

[56] References Cited

U.S. PATENT DOCUMENTS 3,892,790 7/1975 Tobe et al. ..... 260/429 R
3,904,663 9/1975 Tobe et al. ..... 260/429 R

FOREIGN PATENT DOCUMENTS 1432562 4/1976 United Kingdom ..... 424/287

OTHER PUBLICATIONS

Braddock et al., Chem. Bio. Interactions, vol. 11, No. 3, pp. 146–149, (1975).
Belluco, Organometallic and Coordination Chemistry of Platinum, Academic Press, N.Y., pp. 93–95, 547–549, (1974).
Tobe et al., J. of Clin. Hematology & Oncology, vol. 7, No. 1, pp. 129–131 & 133, (1977).
Cleare et al., Bioinorganic Chemistry, vol. 2, pp. 187–210, (1973).
Connors et al., Chem. Biol. Interaction, vol. 5, pp. 415–424, (1972).
Gale et al., Research Communications in Chemical Pathology and Pharmocology, vol. 7, pp. 529–538, (1974).
"American Druggist, Pharmaceutical and Medical Science," pp. 33 & 34, (1969).

*Primary Examiner*—Helen M. S. Sneed
*Attorney, Agent, or Firm*—Cushman, Darby & Cushman

[57] ABSTRACT

This invention relates to a compound of platinum having the structure:

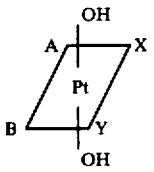

in which X and Y are halogenoid groups which are the same or different and are preferably both chloride but may be other halide or pseudohalide such as cyanate, thiocyanate and azide or other similar groups, and A and B are the same or different branched chain aliphatic amine groups co-ordinated to the Pt through their N atoms.

8 Claims, No Drawings

COMPOSITIONS CONTAINING PLATINUM

Matter enclosed in heavy brackets [ ] appears in the original patent but forms no part of this reissue specification; matter printed in italics indicates the additions made by reissue.

This invention relates to new compositions of matter containing platinum.

According to one aspect of the present invention a composition of matter comprises a co-ordination compound of platinum having the structure:

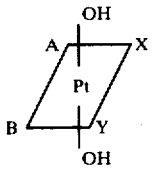

in which X and Y are halogenoid groups which are the same or different and are preferably both chloride but may be other halide or pseudohalide such as cyanate, thiocyanate and azide and A and B are the same or different branched chain aliphatic amine groups co-ordinated to the Pt through their N atoms.

According to a second aspect of the present invention there is provided a co-ordination compound of platinum having the structure:

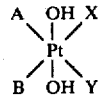

in which X and Y are halogenoid groups which are the same or different and are preferably both chloride but may be other halide pseudohalide such as cyanide, cyanate, thiocyanate, or azide or other similar groups and A and B are the same or different branched chain aliphatic amine groups or C-substituted branched chain aliphatic amine groups co-ordinated to the Pt through their N atoms each having the general formula $$C_nR_{2n+1}NH_2$$

in which n may vary from 3 to 9 and in which all of the R groups are either the same or different and are preferably all hydrogen but may be selected from the group consisting of hydrogen, alkyl, aryl, alkaryl, aralkyl, halogen, pseudohalogen, hydroxy, carbonyl, formyl, nitro, amido, amino, sulphonic acid, sulphonic acid salt, carboxylic acid, carboxylic acid salt, and substituted alkyl, aryl, alkaryl and aralkyl groups.

The platinum is preferably present as $Pt^{4+}$, thus producing a neutral complex with two hydroxyl and two halide ligands.

Although R groups other than hydrogen are not normally preferred, they may be used and may comprise lower alkyl such as methyl or ethyl or a solubilizing group such as a sulphonic acid group. Solubilizing groups as substituents such as carboxylic acid, sulphonic acid, carboxylic acid salt, sulphonic acid salt, e.g. the sodium, potassium or lithium salts are sometimes appropriate when the clinical conditions require high solubility.

Throughout the specification and claims, the term "halogenoid" is used to mean halide (chloride, bromide, iodide or fluoride) or pseudohalide such as cyanide, cyanate, thiocyanate or azide.

Suitable branched chain amine compounds which may be used for groups A and B are isopropylamine, isobutylamine, isoamylamine and 2-aminohexane.

Results obtained using trans di-hydroxo complexes of Pt(IV) where in the above formula X and Y are both chloride and A and B are the same stated branched chain amine are as follows:

| Tumour | A and B | mgm./Kgm $ID_{90}$ | mgm./Kgm $LD_{50}$ | Therapeutic Index (II) |
|---|---|---|---|---|
| ADJ/PC6 | exo 2 amino nor bornane | 40.5 | 660 | 16.3 |
| | ISO propylamine (oil) | 7.5 | 90 | 12.0 |
| | (water) | 4.2 | 54 | 12.9 |
| | ISO Butylamine | 19.5 | 410 | 21 |
| | ISO pentylamine | 112 | 800 | 7.1 |
| | (amylamine) | 19.0 | 20 | 37.9 |
| | | $ED_{90}$ | $LD_{50}$ | TI |
| Walker | ISO propylamine | | | |
| | (oil) | 17 | 45 | 2.6 |
| | (water) | 16 | 56 | 3.5 |

These results were obtained using the standard test protocol for the ADJ/PC6 and Walker tumours on Balb-c white mice.

These series of results obtained using the standard test protocol for the P 388 (ascitic) lymphocytic leukaemia using the isopropylamine complex are as follows:

| Dose mgm/ Kgm | Control Body weight change | Animal weight difference (T − C) | Tumour evaluation Test (days) | Control (Days) (C) | % age Increase in life span (T/C) |
|---|---|---|---|---|---|
| 200 | −1.4 | −4.6 | 6.2 | 15.5 | |
| 100 | −1.4 | −4.0 | 6.4 | 15.5 | |
| 50.0 | −1.4 | −3.6 | 24.0 | 15.5 | 154 |
| 25.0 | −1.4 | −1.6 | 23.3 | 15.5 | 150 |
| 12.5 | −1.4 | −1.8 | 21.3 | 15.5 | 137 |
| 200 | 1.0 | −1.0 | 4.19 | 11.8 | |
| 100 | 1.0 | −6.4 | 6.1 | 11.8 | |
| 50.0 | 1.0 | −6.5 | 8.0 | 11.8 | |
| 25.0 | 1.0 | −5.7 | 15.0 | 11.8 | 127 |
| 12.5 | 1.0 | −4.2 | 21.8 | 11.8 | 184 |
| 200 | 1.0 | −1.0 | 3.0 | 11.8 | |
| 100 | 1.0 | −6.5 | 6.8 | 11.8 | |
| 50.0 | 1.0 | −5.2 | 18.0 | 11.8 | 152 |
| 25.0 | 1.0 | −4.0 | 16.1 | 11.8 | 136 |
| 12.5 | 1.0 | −2.5 | 15.3 | 11.8 | 129 |

Other branched chain amines which may be used as ligands A and B are:

2 amino 5 methylhexane
2 amine 4 methylhexane
2 amino heptane
tert. butylamine

Methods of Preparation

Preferred methods of preparation of trans dihydroxo cis dichloro diamine Pt (IV) complexes (i.e. where A+B in the above defined structure are as follows:

The complexes are prepared by the general method of heating a slurry of the respective cis-diaminedichloroplatinum (II) complex with hydrogen peroxide solution as exemplified below.

Preparation of
cis-Dichloro-trans-dihydroxybis(Isopropylamine)
platinum IV hydrate (1/1)

Recrystallised cis- $[Pt(i\text{-}C_3H_7NH_2)_2Cl_2]$ (26.8 g) was slurried in hot water (50 ml) and aqueous hydrogen peroxide (40% v/v, 100 ml) was added with stirring. The slurry was boiled for 0.5 hours until yellow in colour, chilled, filtered and the residue washed with water, etharal and air dried. The crude product (20 g) was recrystallised from water (285 ml) with hydrogen peroxide solution (15 ml) and dried in vacuo at 100° C. for four hours.

Yield 10.5 g. 35%

| Elemental analysis | C | H | N | O | Cl |
|---|---|---|---|---|---|
| Calculated % | 16.5 | 5.1 | 6.4 | 11.- | 16.3 |
| Found % | 16.6 | 4.8 | 6.4 | 11.7 | 16.1 |

Infra-red spectrum

The hydroxyl stretching absorption ($v_o$—H) occurs at 3515 m $cm^{-1}$

Preparation of
cis-bis(2-amino-5-methylhexane)dichloro-trans
dihydroxy platinum (IV)

Recrystallised cis- $[Pt(C_7H_{15}NH_2)_2Cl_2]$ (15 g) was slurried in warm water (31 ml) and hydrogen peroxide solution (40% v/v,60 ml) was added with stirring. The slurry was boiled for ten minutes, chilled, filtered and the orange product washed with water and dried in vacuo.

Yield 7.4 g. 46%

| Elemental analysis | C | H | N | O | Cl |
|---|---|---|---|---|---|
| Calculated % | 31.7 | 6.8 | 5.3 | 6.0 | 13.4 |
| Found % | 32.1 | 6.7 | 5.5 | 6.2 | 13.6 |

Infra-red Spectrum

The hydroxyl stretching absorption ($v_o$—H) occurs at 3340 mg $cm^{-1}$.

Platinum (IV) complexes are more soluble than Platinum (IV) complexes are more soluble than platinum (II) complexes and, after solubilizing Pt(IV) may be used in the form of Pt(II). The branched chain amine complexes of Pt(IV) are also useful in catalyst preparation by impregnating supports with an aqueous solution of the complex. Alternatively, the solution may be based upon an organic medium. The complexes of the invention may also be used as catalysts in the hydrosilation of organic compounds so as to introduce a silica radical into an organic compound and as synthetic intermediate compounds.

What is claimed is:

1. A co-ordination compound of platinum having the structure:

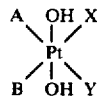

in which X and Y are halogen and A and B are the same or different branched chain aliphatic amine groups or C-substituted branched chain aliphatic amine groups co-ordinated to the Pt through their N atoms each having the general formula $$C_nR_{2n+1}NH_2$$

in which n may vary from 3 to 9 and in which all of the R groups are the same or different and are selected from the group consisting of hydrogen, alkyl, aryl, alkaryl, aralkyl, halogen, pseudohalogen, hydroxy, carbonyl, formyl, nitro, amido, amino, sulphonic acid, sulphonic acid salt, carboxylic acid and carboxylic acid salt.

2. A compound according to claim 1 in which X and Y are both chlorine and R is hydrogen.

3. A compound according to claim 1 wherein the platinum is present as $Pt^{4+}$.

4. A compound according to claim 1 wherein the R groups are the same or different lower alkyl.

5. A compound according to claim 1 wherein A and B are isopropylamine, isobutylamine, isoamylamine and 2-aminohexane.

6. A composition comprising a co-ordination compound of platinum having the structures:

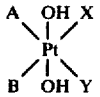

in which X and Y are halogen and A and B are exo 2 amino norbornane.

*7. The compound cis-dichloro-trans-dihydroxybis (isopropylamine) platinum IV hydrate.*

*8. A compound according to claim 1 wherein X and Y are both chlorine and A and B are both isopropylamine.*

* * * * *